United States Patent
Sianawati et al.

(10) Patent No.: US 9,510,597 B2
(45) Date of Patent: Dec. 6, 2016

(54) MICROBICIDAL COMPOSITION

(71) Applicants: Dow Global Technologies LLC, Midland, MI (US); Rohm and Haas Company, Philadelphia, PA (US)

(72) Inventors: Emerentiana Sianawati, Vernon Hills, IL (US); Jon B. Raymond, Buffalo Grove, IL (US)

(73) Assignees: Dow Global Technologies LLC, Midland, MI (US); Rohm and Haas Company, Philadelphia, PA (US)

( * ) Notice: Subject to any disclaimer, the term of this patent is extended or adjusted under 35 U.S.C. 154(b) by 11 days.

(21) Appl. No.: 14/402,984

(22) PCT Filed: May 22, 2013

(86) PCT No.: PCT/US2013/042185
§ 371 (c)(1),
(2) Date: Nov. 21, 2014

(87) PCT Pub. No.: WO2013/177258
PCT Pub. Date: Nov. 28, 2013

(65) Prior Publication Data
US 2015/0164077 A1  Jun. 18, 2015

Related U.S. Application Data

(60) Provisional application No. 61/651,170, filed on May 24, 2012.

(51) Int. Cl.
| | | |
|---|---|---|
| *A01N 43/32* | (2006.01) | |
| *A01N 43/40* | (2006.01) | |
| *A01N 43/70* | (2006.01) | |
| *A01N 43/80* | (2006.01) | |
| *A01N 31/08* | (2006.01) | |
| *A01N 33/20* | (2006.01) | |
| *A01N 47/44* | (2006.01) | |

(52) U.S. Cl.
CPC .............. *A01N 43/80* (2013.01); *A01N 31/08* (2013.01); *A01N 33/20* (2013.01); *A01N 43/32* (2013.01); *A01N 43/40* (2013.01); *A01N 43/70* (2013.01); *A01N 47/44* (2013.01)

(58) Field of Classification Search
CPC ........ A01N 43/80; A01N 31/08; A01N 33/20; A01N 43/40; A01N 43/70; A01N 47/44; A01N 43/32
See application file for complete search history.

(56) References Cited

U.S. PATENT DOCUMENTS

| | | | |
|---|---|---|---|
| 5,380,624 A | 1/1995 | Yoshida et al. | |
| 7,455,851 B1 * | 11/2008 | Nelson | A01N 43/40 424/405 |
| 2003/0187095 A1 | 10/2003 | Cornish et al. | |
| 2004/0014799 A1 | 1/2004 | Antoni-Zimmermann et al. | |
| 2007/0078118 A1 | 4/2007 | Levy et al. | |
| 2008/0167374 A1 * | 7/2008 | Stickler | A01N 25/22 514/530 |
| 2008/0227755 A1 | 9/2008 | Sloan | |
| 2008/0227766 A1 | 9/2008 | Wunder et al. | |
| 2010/0189811 A1 | 7/2010 | Baum et al. | |
| 2010/0239679 A1 * | 9/2010 | Greene | A01N 25/26 424/490 |
| 2010/0260813 A1 | 10/2010 | Schnabel et al. | |
| 2011/0015299 A1 | 1/2011 | Annis et al. | |
| 2012/0184436 A1 | 7/2012 | Yin | |
| 2013/0064899 A1 | 3/2013 | Schmidt et al. | |

FOREIGN PATENT DOCUMENTS

| | | |
|---|---|---|
| WO | 2008148855 A1 | 12/2008 |

OTHER PUBLICATIONS

Schwalbe et al. (Antimicrobial Susceptibility Testing Protocols 2007, CRC Press p. 276).*

* cited by examiner

*Primary Examiner* — Ernst V Arnold
(74) *Attorney, Agent, or Firm* — Kenneth Crimaldi

(57) ABSTRACT

Synergistic microbicidal compositions containing N-methyl-1,2-benzisothiazolin-3-one and dodecylguanidine, poly(hexamethylene biguanide hydrochloride), sodium pyrithione, sodium ortho-phenylphenate, terbutryn, dimethoxane or 2-(hydroxymethyl)-2-nitropropane-1,3-diol.

7 Claims, No Drawings

MICROBICIDAL COMPOSITION

This invention relates to a synergistic combination of selected microbicides having greater activity than would be observed for the individual microbicides.

In some cases, commercial microbicides cannot provide effective control of microorganisms, even at high use concentrations, due to weak activity against certain types of microorganisms, e.g., those resistant to some microbicides, or due to aggressive environmental conditions. Combinations of different microbicides are sometimes used to provide overall control of microorganisms in a particular end use environment. For example, U.S. Pat. App. Pub. No. 2007/0078118 discloses synergistic combinations of N-methyl-1,2-benzisothiazolin-3-one (MBIT) with other biocides. However, there is a need for additional combinations of microbicides having enhanced activity against various strains of microorganisms to provide effective control of the microorganisms. Moreover, there is a need for combinations containing lower levels of individual microbicides for environmental and economic benefit. The problem addressed by this invention is to provide such additional combinations of microbicides.

STATEMENT OF THE INVENTION

The present invention is directed to a synergistic microbicidal composition comprising: (a) N-methyl-1,2-benzisothiazolin-3-one; and (b) at least one microbicide selected from the group consisting of dodecylguanidine, poly(hexamethylene biguanide hydrochloride), sodium pyrithione, sodium ortho-phenylphenate, terbutryn, dimethoxane and 2-(hydroxymethyl)-2-nitropropane-1,3-diol.

DETAILED DESCRIPTION OF THE INVENTION

As used herein, the following terms have the designated definitions, unless the context clearly indicates otherwise. "MBIT" is N-methyl-1,2-benzisothiazolin-3-one. "Dimethoxane" is 2,6-dimethyl-1,3-dioxan-4-ol acetate. The term "microbicide" refers to a compound capable of killing, inhibiting the growth of or controlling the growth of microorganisms at a locus; microbicides include bactericides, fungicides and algaecides. The term "microorganism" includes, for example, fungi (such as yeast and mold), bacteria and algae. The term "locus" refers to an industrial system or product subject to contamination by microorganisms. The following abbreviations are used throughout the specification: ppm=parts per million by weight (weight/weight), mL=milliliter, ATCC=American Type Culture Collection, MBC=minimum biocidal concentration, and MIC=minimum inhibitory concentration. Unless otherwise specified, temperatures are in degrees centigrade (° C.), and references to percentages are by weight (wt %). Amounts of organic microbicides are given on an active ingredient basis in ppm (w/w).

The compositions of the present invention unexpectedly have been found to provide enhanced microbicidal efficacy at a combined active ingredient level lower than that of the individual microbicides. Additional microbicides beyond those listed in the claims may be present in the composition.

In one preferred embodiment of the invention, the antimicrobial composition comprises N-methyl-1,2-benzisothiazolin-3-one and dodecylguanidine, and a ratio of N-methyl-1,2-benzisothiazolin-3-one to dodecylguanidine is from 1:1 to 1:650, preferably from 1:1 to 1:30 or from 1:50 to 1:650, preferably from 1:3 to 1:30 or from 1:80 to 1:650, preferably from 1:3.5 to 1:28 or from 1:80 to 1:640.

In one preferred embodiment of the invention, the antimicrobial composition comprises N-methyl-1,2-benzisothiazolin-3-one and poly(hexamethylene biguanide hydrochloride), and a ratio of N-methyl-1,2-benzisothiazolin-3-one to poly(hexamethylene biguanide hydrochloride) is from 4:1 to 2:1 or from 1:533 to 1:1067.

In one preferred embodiment of the invention, the antimicrobial composition comprises N-methyl-1,2-benzisothiazolin-3-one and sodium pyrithione, and a ratio of N-methyl-1,2-benzisothiazolin-3-one to sodium pyrithione is from 21:1 to 1:40, preferably from 5:1 to 1:40, preferably from 3.3:1 to 1:35.

In one preferred embodiment of the invention, the antimicrobial composition comprises N-methyl-1,2-benzisothiazolin-3-one and sodium ortho-phenylphenate, and a ratio of N-methyl-1,2-benzisothiazolin-3-one to sodium ortho-phenylphenate is from 1:60 to 1:135, preferably from 1:60 to 1:130, preferably from 1:62.5 to 1:125.

In one preferred embodiment of the invention, the antimicrobial composition comprises N-methyl-1,2-benzisothiazolin-3-one and terbutryn, and a ratio of N-methyl-1,2-benzisothiazolin-3-one to terbutryn is from 1:100 to 1:110,000, preferably from 1:104 to 1:106,667.

In one preferred embodiment of the invention, the antimicrobial composition comprises N-methyl-1,2-benzisothiazolin-3-one and dimethoxane, and a ratio of N-methyl-1,2-benzisothiazolin-3-one to dimethoxane is from 1:1 to 1:650, preferably from 1:1 to 1:30 or from 1:50 to 1:650, preferably from 1:3 to 1:30 or from 1:80 to 1:650, preferably from 1:3.5 to 1:28 or from 1:80 to 1:640.

In one preferred embodiment of the invention, the antimicrobial composition comprises N-methyl-1,2-benzisothiazolin-3-one and 2-(hydroxymethyl)-2-nitropropane-1,3-diol. Preferably, a weight ratio of a ratio of N-methyl-1,2-benzisothiazolin-3-one to 2-(hydroxymethyl)-2-nitropropane-1,3-diol is from 3:1 to 1:5, preferably from 2:1 to 1:4.

The microbicides in the composition of this invention may be used "as is" or may first be formulated with a solvent or a solid carrier. Suitable solvents include, for example, water; glycols, such as ethylene glycol, propylene glycol, diethylene glycol, dipropylene glycol, polyethylene glycol, and polypropylene glycol; glycol ethers; alcohols, such as methanol, ethanol, propanol, phenethyl alcohol and phenoxypropanol; ketones, such as acetone and methyl ethyl ketone; esters, such as ethyl acetate, butyl acetate, triacetyl citrate, and glycerol triacetate; carbonates, such as propylene carbonate and dimethyl carbonate; and mixtures thereof. It is preferred that the solvent is selected from water, glycols, glycol ethers, esters and mixtures thereof. Suitable solid carriers include, for example, cyclodextrin, silicas, diatomaceous earth, waxes, cellulosic materials, alkali and alkaline earth (e.g., sodium, magnesium, potassium), montmorillonite, zeolite, layered double hydroxide metal salts (e.g., chloride, nitrate, bromide, sulfate) and charcoal.

A microbicide component can be formulated in the form of an emulsion, dispersion or solution. The solvent component can be an organic solvent or water, preferably water. Such mixtures can contain adjuvants, co-solvents, thickeners, anti-freeze agents, emulsifiers, dispersants, fillers, pigments, surfactants, biodispersants, defoamers, sulfosuccinates, terpenes, furanones, polycations, stabilizers, scale inhibitors and anti-corrosion additives.

When both microbicides are each first formulated with a solvent, the solvent used for the first microbicide may be the same as or different from the solvent used to formulate the other commercial microbicide, although water is preferred for most industrial biocide applications. It is preferred that the two solvents are miscible.

Those skilled in the art will recognize that the microbicide components of the present invention may be added to a locus sequentially, simultaneously, or may be combined before being added to the locus. It is preferred that the first microbicide and the second microbicide component be added to a locus simultaneously or sequentially. When the microbicides are added simultaneously or sequentially, each individual component may contain adjuvants, solvent, thickeners, anti-freeze agents, colorants, sequestrants (such as ethylenediamine-tetraacetic acid, ethylenediaminedisuccinic acid, iminodisuccinic acid and salts thereof), dispersants, surfactants, biodispersants, sulfosuccinates, terpenes, furanones, polycations, stabilizers, scale inhibitors and anti-corrosion additives.

The microbicidal compositions of the present invention can be used to inhibit the growth of microorganisms or higher forms of aquatic life (such as protozoans, invertebrates, bryozoans, dinoflagellates, crustaceans, mollusks, etc.) by introducing a microbicidally effective amount of the compositions onto, into, or at a locus subject to microbial attack. Suitable loci include, for example: industrial process water; electrocoat deposition systems; cooling towers; air washers; gas scrubbers; mineral slurries; wastewater treatment; ornamental fountains; reverse osmosis filtration; ultrafiltration; ballast water; evaporative condensers; heat exchangers; pulp and paper processing fluids and additives; starch; plastics; emulsions; dispersions; paints; latices; coatings, such as varnishes; construction products, such as mastics, caulks, and sealants; construction adhesives, such as ceramic adhesives, carpet backing adhesives, and laminating adhesives; industrial or consumer adhesives; photographic chemicals; printing fluids, colorants; household products, such as bathroom and kitchen cleaners and sanitary wipes; cosmetics; toiletries; shampoos; soaps; detergents; industrial cleaners; floor polishes; laundry rinse water; metalworking fluids; conveyor lubricants; hydraulic fluids; leather and leather products; textiles; textile products; wood and wood products, such as plywood, chipboard, wallboard, flakeboard, laminated beams, oriented strandboard, hardboard, and particleboard; petroleum processing fluids; fuel; oilfield fluids, such as injection water, fracture fluids, and drilling muds; agriculture adjuvant preservation; preservation of agricultural products, surfactant preservation; medical devices; diagnostic reagent preservation; food preservation, such as plastic or paper food wrap; food, beverage, and industrial process pasteurizers; toilet bowls; recreational water; pools; and spas.

Preferably, the microbicidal compositions of the present invention are used to inhibit the growth of microorganisms at a locus selected from one or more of mineral slurries, pulp and paper processing fluids and additives, starch, emulsions, dispersions, paints, latices, coatings, construction adhesives, such as ceramic adhesives, carpet backing adhesives, photographic chemicals, printing fluids, colorants, household products such as bathroom and kitchen cleaners and sanitary wipes, cosmetics, toiletries, shampoos, soaps, detergents, industrial cleaners, floor polishes, laundry rinse water, metal working fluids, textile products, wood and wood products, preservation of agricultural products and agricultural adjuvants, surfactant preservation, diagnostic reagent preservation, food preservation, and food, beverage, and industrial process pasteurizers.

The specific amount of the composition of this invention necessary to inhibit or control the growth of microorganisms and higher aquatic life forms in a locus depends upon the particular locus to be protected. Typically, the amount of the composition of the present invention to control the growth of microorganisms in a locus is sufficient if it provides from 0.1 to 1,000 ppm of the isothiazoline ingredient of the composition in the locus. It is preferred that the isothiazolone ingredients of the composition be present in the locus in an amount of at least 0.5 ppm, preferably at least 4 ppm, preferably at least 10 ppm. It is preferred that the isothiazolone ingredients of the composition be present in the locus in an amount of no more than 1000 ppm, preferably no more than 500 ppm, preferably no more than 200 ppm, preferably no more than 100 ppm.

Examples

The synergism of the biocides combination of the present invention was determined using the method described by Kull, F. C, et. all in *Applied Microbiology* 9:538-541 (1961). The formula to calculate the synergistic index (SI) is $$Qa/QA+Qb/QB=SI$$

Where

QA=concentration of compound A in ppm, acting alone produced an end point or if end point could not be established, the highest concentration tested will be used the as the end point for the calculation and the SI will be recorded in "less than or <" values Qa=concentration of compound A in ppm, in the mixture, which produced an end point QB=concentration of compound B in ppm, acting alone produced an end point or if end point could not be established, the highest concentration tested will be used the as the end point for the calculation and the SI will be recorded in "less than or <" values Qb=concentration of compound B in ppm, in the mixture, which produced an end point Synergism within two biocides is demonstrated when the SI has a value less than 1. The mixtures showed an additive effect if SI is equal to 1 and antagonistic if SI is greater than 1. In this invention, two different approaches of synergistic study were conducted. One synergistic study is determined based on the minimum inhibitory concentration (MIC), the lowest concentration of a biocide prevents the growth of tested microorganism under a specific set of conditions. The second study was based on three to four consecutive challenge testing. This test was conducted to take biocide mode of action and speed of kill into a consideration. The data for synergistic effect was depicted at any point of in each challenge testing where the synergistic effect was observed and showed the most activities.

The microorganisms tested are *Escherichia coli* (*E. coli*, ATCC #8739), yeast, *Candida albicans* (*c. albicans*, ATCC #10231) and mold, *Aspergillus niger* (*a. niger*, ATCC #16404). The final concentration of microorganisms in the tested media is about $10^4$ cfu/mL Experimental Method 1

Minimum Inhibitory Concentration (MIC)

MBIT synergy with a secondary biocide was determined by evaluating the minimum biocide or biocide blend concentration required to inhibit microbial growth. All studies were conducted using a 96 well microtiter plate format. For all studies, 200 µl of microbial growth media, containing various concentrations of MBIT alone, the secondary biocide alone, or combinations of both biocide chemistries, was added to individual wells of a microtiter plate. Specifically, Tryptic Soy Broth (TSB) was utilized for bacteria (*E. coli*, ATCC #8739), Yeast Malt Extract Broth (YMB) for yeast (*Candida albicans*, ATCC #10231) and Potato Dextrose Broth (PDB) for mold (*Aspergillus niger*, ATCC #16404). Test organisms, at a final concentration of $10^4$ CFU/mL or $10^4$ spores/mL, were applied to each well in parallel experiments to initiate the MIC evaluations. Growth medium containing no biocide was utilized as a control in each experimental setup to confirm the growth viability of each organism. Eight concentrations (2-fold dilutions) of each individual biocide were evaluated in the microbial growth inhibition studies in addition to the 64 possible combinations of these biocide concentrations. Evaluation of the individual biocide concentrations is required to achieve an inhibitory concentration end point for synergy index calculation. Following organism addition the 96-well microtiter plates were incubated at 25° C. for 48 hours or until growth was observed in the control wells containing no biocide. Individual wells were scored as growth or no growth based on visual organism growth turbidity. The lowest single active biocide concentrations resulting in no organism growth, for both MBIT and the secondary biocide, were recorded for synergy index calculations in addition to the combined biocide concentrations which resulted in an inhibition of microbial growth.

Ratios of the two biocides exhibiting synergy are presented in Tables 1-6.

TABLE 1

Synergistic effect of MBIT with Dodecylguanidine

| Active Weight ratio of MBIT to Dodecylguanidine hydrochloride (DDG) | Minimum Inhibitory Concentration (ppm) | | Synergy Index |
|---|---|---|---|
| | MBIT | DDG | |
| *E. coli* | | | |
| 1:0 | 62.5 | | |
| 0:1 | | 875 | |
| 1:7 | 31.25 | 218.75 | 0.75 |
| 1:3.5 | 31.25 | 109.3 | 0.63 |
| 1:28 | 15.63 | 437.5 | 0.75 |
| 1:14 | 15.63 | 218.75 | 0.50 |
| *C. albicans* | | | |
| 1:0 | 6.25 | | |
| 0:1 | | 2000 | |
| 1:160 | 3.13 | 500 | 0.75 |
| 1:80 | 3.13 | 259 | 0.63 |
| 1:640 | 1.56 | 1000 | 0.75 |
| *A. niger* | | | |
| 1:0 | 10 | | |
| 0:1 | | 750 | |
| 1:300 | 1.25 | 375 | 0.63 |
| 1:150 | 2.5 | 375 | 0.75 |

TABLE 2

Synergistic effect of MBIT with Polyhexamethylene biguanide

| Active Weight ratio of MBIT to Polyhexamethylene biguanide (PHMB) | Minimum Inhibitory Concentration (ppm) | | Synergy Index |
|---|---|---|---|
| | MBIT | PHMB | |
| *E. coli* | | | |
| 1:0 | 12.5 | | |
| 0:1 | | 1.6 | |
| 2:1 | 1.6 | 0.8 | 0.628 |
| 4:1 | 3.1 | 0.8 | 0.748 |
| *C. albicans* | | | |
| 1:0 | 0.3125 | | |
| 0:1 | | 100 | |
| 1:533 | 0.094 | 50 | 0.75 |
| 1:1067 | 0.047 | 50 | 0.63 |
| *A. niger*: No synergy at any ratio | | | |

TABLE 3

Synergistic effect of MBIT with Sodium Pyrithione

| Active Weight ratio of MBIT to Sodium pyrithione (NaPT) | Minimum Inhibitory Concentration (ppm) | | Synergy Index |
|---|---|---|---|
| | MBIT | NaPT | |
| *E. coli* | | | |
| 1:0 | 25 | | |
| 0:1 | | 2.5 | |
| 21:1 | 12.5 | 0.6 | 0.75 |
| *C. albicans*: No synergy at any ratio | | | |
| *A. niger* | | | |
| 1:0 | 6.3 | | |
| 0:1 | | 25 | |
| 1:35 | 0.2 | 7.5 | 0.53 |
| 1:19 | 0.4 | 7.5 | 0.56 |
| 1:9.4 | 0.8 | 7.5 | 0.63 |
| 1:5 | 1.56 | 7.5 | 0.75 |
| 1:5 | 0.8 | 3.75 | 0.38 |
| 1:2.4 | 1.56 | 3.75 | 0.51 |
| 1:1.2 | 3.12 | 3.75 | 0.75 |
| 1.7:1 | 3.13 | 1.88 | 0.62 |
| 3.3:1 | 3.12 | 0.95 | 0.55 |

TABLE 4

Synergistic effect of MBIT with Sodium o-Phenyl Phenate

| Active Weight ratio of MBIT and sodium Ortho Phenyl phenate (NaOPP) | Minimum Inhibitory Concentration (ppm) | | Synergy Index |
|---|---|---|---|
| | MBIT | NaOPP | |
| *E. coli*: No synergy at any ratio | | | |
| *C. albicans*: No synergy at any ratio | | | |
| *A. niger* | | | |
| 1:0 | 6.3 | | |
| 0:1 | | 200 | |
| 1:62.5 | 1.6 | 100 | 0.75 |
| 1:125 | 0.8 | 100 | 0.63 |

TABLE 5

Synergistic effect of MBIT with Terbutryn

| Active Weight ratio of MBIT and Terbutryn | Minimum Inhibitory Concentration (ppm) | | Synergy Index |
|---|---|---|---|
| | MBIT | Terbutryn | |
| *E. coli*: No synergy at any ratio | | | |
| *C. albicans* | | | |
| 1:0 | 3 | | |
| 0:1 | | >20000 | |
| 1:6,667 | 1.5 | 10,000 | <1 |
| 1:3,333 | 1.5 | 5,000 | <0.75 |
| 1:1,667 | 1.5 | 2,500 | <0.63 |
| 1:833 | 1.5 | 1,250 | <0.56 |
| 1:417 | 1.5 | 625 | <0.53 |
| 1:208 | 1.5 | 312.5 | <0.52 |
| 1:104 | 1.5 | 156.25 | <0.51 |
| 1:13,333 | 0.75 | 10,000 | <0.75 |
| 1:6,667 | 0.75 | 5,000 | <0.5 |
| 1:3,333 | 0.75 | 2,500 | <0.375 |
| 1:1,667 | 0.75 | 1,250 | <0.31 |
| 1:833 | 0.75 | 625 | <0.281 |
| 1:417 | 0.75 | 312.5 | <0.27 |
| 1:26,667 | 0.375 | 10,000 | <0.63 |
| 1:13,333 | 0.375 | 5,000 | <0.38 |
| 1:53,333 | 0.188 | 10,000 | <0.56 |
| 1:26,667 | 0.188 | 5,000 | <0.31 |
| 1:213,333 | 0.094 | 20,000 | <1.03 |
| 1:106,667 | 0.094 | 10,000 | <0.53 |
| 1:53,333 | 0.094 | 5,000 | <0.56 |
| 1:213,333 | 0.047 | 10,000 | <0.52 |
| 1:106,667 | 0.047 | 5,000 | <0.41 |

TABLE 6

Synergistic effect of MBIT with 4-chloro-3,5-xylenol

| Active Weight ratio of MBIT and 4-chloro-3,5-xylenol or chloroxylenol (PCMX) | Minimum Inhibitory Concentration (ppm) | | Synergy Index |
|---|---|---|---|
| | MBIT | PCMX | |
| *E. coli*: No synergy at any ratio | | | |
| *C. albicans*: No synergy at any ratio | | | |
| *A. niger*: No synergy at any ratio | | | |

Experimental Method 2

Minimum Kill Concentration (MKC)

MKC evaluations were utilized to determine the synergy of MBIT with the co-biocides DXN (6-Acetoxy-2,4-dimethyl-m-dioxane) and THNM (2-Hydroxymethyl-2-nitro-1,3-propanediol) due to the inability to evaluate these particular biocide chemistries in MIC evaluations. The following test methods were designed for the evaluation of the aforementioned synergistic combinations. The results can be found in Tables 7 and 8.

Bacteria

Testing began (day 0) by applying sterile water, supplemented with 2.0% TSB, to each well of a 96-well microtiter plate. Various concentrations of MBIT alone, the co-biocide alone, or combinations of both biocide chemistries, were added to individual wells of the microtiter plate followed by addition of *Escherichia coli* (ATCC #8739) at a final concentration of $5 \times 10^4$ CFU/mL. Equivalent inoculations were applied on days 7, 14 and 21 of the study. To determine the extent of bacterial kill, an aliquot (20 µl) of each sample was taken on days 1, 7, 8, 14, 15, 21, 22 and transferred to tryptic soy broth (180 µl). After 48 hours of incubation at 30° C., bacterial kill (to a maximum detection limit of $5 \times 10^1$ CFU/mL) was visually determined by the presence or lack of turbidity within the TSB.

Yeast

Testing began (day 0) by applying sterile water, supplemented with 2.0% yeast malt extract broth, to each well of a 96-well microtiter plate. Various concentrations of MBIT alone, the co-biocide alone, or combinations of both biocide chemistries, were added to individual wells of the microtiter plate followed by addition of *Candida albicans* (ATCC #10231) at a final concentration of $5 \times 10^4$ CFU/mL. Equivalent inoculations were applied on days 7, 14 and 21 of the study. To determine the extent of yeast kill, an aliquot (20 µl) of each sample was taken on days 1, 7, 8, 14, 15, 21, 22 and transferred to yeast malt extract broth (180 µl). After 48 hours of incubation at 30° C., yeast kill (to a maximum detection limit of $5 \times 10^1$ CFU/mL) was visually determined by the presence or lack of turbidity within the YMB.

Mold

Testing began (day 0) by applying sterile water, supplemented with 2.0% potato dextrose broth, to each well of a 96-well microtiter plate. Various concentrations of MBIT alone, the co-biocide alone, or combinations of both biocide chemistries, were added to individual wells of the microtiter plate followed by addition of *Aspergillus niger* (ATCC #16404) at a final concentration of $5 \times 10^4$ spores/mL. Equivalent inoculations were applied on days 7 and 14 of the study. To determine the extent of mold kill, an aliquot (20 µl)

of each sample was taken on days 1, 7, 8, 14, 15, 21 and transferred to potato dextrose broth (180 μl). After 48-96 hours of incubation at 30° C., mold kill (to a maximum detection limit of $5 \times 10^1$ spores/mL) was visually determined by the presence or lack of turbidity within the PDB.

TABLE 7

Synergistic effect of MBIT with Dimethoxane

| Active Weight ratio of MBIT and Dimethoxane | Minimum Inhibitory Concentration (ppm) | | Synergy Index |
|---|---|---|---|
| | MBIT | DXN | |
| Synergistic kill of *E. coli* at day 7 | | | |
| 1:0 | 62.5 | | |
| 0:1 | | 875 | |
| 1:7 | 31.25 | 218.75 | 0.75 |
| 1:3.5 | 31.25 | 109.3 | 0.63 |
| 1:28 | 15.63 | 437.5 | 0.75 |
| 1:14 | 15.63 | 218.75 | 0.50 |
| Synergistic kill of *C. albicans* at day 21 | | | |
| 1:0 | 6.25 | | |
| 0:1 | | 2000 | |
| 1:160 | 3.13 | 500 | 0.75 |
| 1:80 | 3.13 | 259 | 0.63 |
| 1:640 | 1.56 | 1000 | 0.75 |
| Synergistic kill of *A. niger* at Day 21 | | | |
| 1:0 | 10 | | |
| 0:1 | | 750 | |
| 1:300 | 1.25 | 375 | 0.63 |
| 1:150 | 2.5 | 375 | 0.75 |

TABLE 8

Synergistic effect of MBIT with 2-(Hydroxymethyl)-2-nitropropane-1,3-diol

| Active Weight ratio of MBIT and 2-(Hydroxymethyl)-2-nitropropane-1,3-diol (THNM) | Minimum Inhibitory Concentration (ppm) | | Synergy Index |
|---|---|---|---|
| | MBIT | THMN | |
| Synergistic kill of *E. coli* at day 21 | | | |
| 1:0 | 125 | | |
| 0:1 | | 125 | |
| 2:1 | 62.5 | 93.75 | 0.75 |
| 1:1 | 31.25 | 62.5 | 0.50 |

TABLE 8-continued

Synergistic effect of MBIT with 2-(Hydroxymethyl)-2-nitropropane-1,3-diol

| Active Weight ratio of MBIT and 2-(Hydroxymethyl)-2-nitropropane-1,3-diol (THNM) | Minimum Inhibitory Concentration (ppm) | | Synergy Index |
|---|---|---|---|
| | MBIT | THMN | |
| 1:2 | 15.63 | 46.88 | 0.38 |
| 1:4 | 15.63 | 78.13 | 0.63 |
| No synergistic kill of *C. albicans* | | | |
| No synergistic kill of *A. niger* | | | |

The invention claimed is:

1. A microbicidal composition comprising:
   (a) N-methyl-1,2-benzisothiazolin-3-one; and
   (b) at least one microbicide selected from the group consisting of dodecylguanidine, poly(hexamethylene biguanide hydrochloride), sodium ortho-phenylphenate, terbutryn, dimethoxane and 2-(hydroxymethyl)-2-nitropropane-1,3-diol; wherein a ratio of N-methyl-1,2-benzisothiazolin-3-one to dodecylguanidine is from 1:1 to 1:650, a ratio of N-methyl-1,2-benzisothiazolin-3-one to poly(hexamethylene biguanide hydrochloride) is from 4:1 to 2:1 or from 1:533 to 1:1067, a ratio of N-methyl-1,2-benzisothiazolin-3-one to sodium ortho-phenylphenate is from 1:60 to 1:135, a ratio of N-methyl-1,2-benzisothiazolin-3-one to terbutryn is from 1:100 to 1:110,000, a ratio of N-methyl-1,2-benzisothiazolin-3-one to dimethoxane is from 1:1 to 1:650 and a ratio of N-methyl-1,2-benzisothiazolin-3-one to 2-(hydroxymethyl)-2-nitropropane-1,3-diol is from 3:1 to 1:5.

2. The microbicidal composition of claim 1 in which said at least one microbicide is dodecylguanidine.

3. The microbicidal composition of claim 1 in which said at least one microbicide is poly(hexamethylene biguanide hydrochloride).

4. The microbicidal composition of claim 1 in which said at least one microbicide is sodium ortho-phenylphenate.

5. The microbicidal composition of claim 1 in which said at least one microbicide is terbutryn.

6. The microbicidal composition of claim 1 in which said at least one microbicide is dimethoxane.

7. The microbicidal composition of claim 1 in which said at least one microbicide is 2-(hydroxymethyl)-2-nitropropane-1,3-diol.

* * * * *